United States Patent
Agris, III et al.

(10) Patent No.: US 11,083,836 B2
(45) Date of Patent: Aug. 10, 2021

(54) SYSTEM AND METHOD FOR MEDICAL FLUID IDENTIFICATION AND VERIFICATION

(71) Applicant: Jacob Agris, Great Neck, NY (US)

(72) Inventors: Jacob Agris, III, Great Neck, NY (US); Arthur E. Uber, III, Pittsburgh, PA (US); Ralph H. Schriver, Tarentum, PA (US); Evelina Zapatka, Upper St. Clair, PA (US); Michael A. Spohn, Fenelton, PA (US)

(*) Notice: Subject to any disclaimer, the term of this patent is extended or adjusted under 35 U.S.C. 154(b) by 751 days.

(21) Appl. No.: 15/038,493

(22) PCT Filed: Nov. 25, 2014

(86) PCT No.: PCT/US2014/067435
§ 371 (c)(1),
(2) Date: May 23, 2016

(87) PCT Pub. No.: WO2015/081109
PCT Pub. Date: Jun. 4, 2015

(65) Prior Publication Data
US 2016/0296692 A1    Oct. 13, 2016

Related U.S. Application Data

(60) Provisional application No. 61/909,109, filed on Nov. 26, 2013.

(51) Int. Cl.
*A61M 5/00* (2006.01)
*A61M 5/172* (2006.01)
*A61M 5/14* (2006.01)

(52) U.S. Cl.
CPC .......... *A61M 5/007* (2013.01); *A61M 5/1723* (2013.01); *A61M 2005/1403* (2013.01);
(Continued)

(58) Field of Classification Search
CPC .. A61M 2005/1403; A61M 2205/3306; A61M 2205/3334; A61M 2205/60; A61M 2205/6063; A61M 5/007; A61M 5/1723
See application file for complete search history.

(56) References Cited

U.S. PATENT DOCUMENTS

| 4,053,433 A | 10/1977 | Lee |
| 4,306,993 A | 12/1981 | Danielson et al. |

(Continued)

OTHER PUBLICATIONS

"Jun. 9, 2016 IPRP from PCT/US2014/067435", dated Jun. 9, 2016.
(Continued)

*Primary Examiner* — Michael T Rozanski
(74) *Attorney, Agent, or Firm* — The Webb Law Firm; Neil Friedrich (57) ABSTRACT

A system for injecting fluid to a patient is provided. The system provides manual or automatic verification and identification of the fluid to be injected, prior to, during or after injection. The system includes: a fluid having at least one active compound and at least one tracer compound; an injector configured to deliver the fluid to the patient through a fluid path set; at least one sensor coupled to at least one of the syringe, the injector, or the patient, configured to measure at least one property of the tracer in the fluid, and a feedback path to adjust at least one injection parameter of the injector based on at least one measurement from the at least one sensor.

19 Claims, 5 Drawing Sheets (52) U.S. Cl.
CPC ........... *A61M 2205/3306* (2013.01); *A61M 2205/3334* (2013.01); *A61M 2205/60* (2013.01); *A61M 2205/6063* (2013.01)

(56) References Cited

U.S. PATENT DOCUMENTS

| | | | |
|---|---|---|---|
| 4,329,393 A | 5/1982 | Laperre et al. |
| 4,390,452 A | 6/1983 | Stevens |
| 4,399,226 A | 8/1983 | Danielson et al. |
| 4,465,473 A | 8/1984 | Ruegg |
| 4,469,623 A | 9/1984 | Danielson et al. |
| 4,767,205 A | 8/1988 | Schwartz et al. |
| 4,939,372 A | 7/1990 | Schvoerer et al. |
| 5,333,044 A | 7/1994 | Shaffer |
| 5,383,858 A | 1/1995 | Reilly et al. |
| 5,759,683 A | 6/1998 | Boswell |
| 6,087,940 A | 7/2000 | Caperna et al. |
| 6,114,038 A | 9/2000 | Castro et al. |
| 6,162,550 A | 12/2000 | Pinchen et al. |
| 6,309,690 B1 | 10/2001 | Brogger et al. |
| 6,432,715 B1 | 8/2002 | Nelson et al. |
| 6,455,157 B1 | 9/2002 | Simons |
| 6,501,825 B2 | 12/2002 | Kaiser et al. |
| 6,527,907 B2 | 3/2003 | Pinchen et al. |
| 6,576,155 B1 | 6/2003 | Barbera-Guillem |
| 6,610,351 B2 | 8/2003 | Shchegolikhin et al. |
| 6,627,031 B1 | 9/2003 | Pinchen et al. |
| 6,647,649 B2 | 11/2003 | Hunt et al. |
| 6,669,663 B1 | 12/2003 | Thompson |
| 6,692,031 B2 | 2/2004 | McGrew |
| 6,819,244 B2 | 11/2004 | Dukler et al. |
| 6,835,326 B2 | 12/2004 | Barbera-Guillem |
| 6,922,146 B2 | 7/2005 | Yogev et al. |
| 7,038,766 B2 | 5/2006 | Kerns et al. |
| 7,041,362 B2 | 5/2006 | Barbera-Guillem |
| 7,055,691 B2 | 6/2006 | Safian |
| 7,057,198 B2 | 6/2006 | Meinhart et al. |
| 7,204,421 B2 | 4/2007 | Austin |
| 7,279,234 B2 | 10/2007 | Dean |
| 7,288,320 B2 | 10/2007 | Steenblik et al. |
| 7,394,997 B2 | 7/2008 | Mei et al. |
| 7,501,092 B2 | 3/2009 | Chen |
| 7,507,588 B2 | 3/2009 | Mehrpouyan et al. |
| 7,623,621 B1 | 11/2009 | Schramm, Jr. |
| 7,674,532 B2 | 3/2010 | Einhorn et al. |
| 7,720,254 B2 | 5/2010 | Stierman et al. |
| 7,745,091 B2 | 6/2010 | True |
| 7,745,092 B2 | 6/2010 | True |
| 7,781,227 B2 | 8/2010 | Mehrpouyan et al. |
| 7,785,717 B2 | 8/2010 | Barbera-Guillem |
| 7,799,568 B2 | 9/2010 | Charles et al. |
| 7,831,042 B2 | 11/2010 | Stierman et al. |
| 7,834,468 B2 | 11/2010 | Dutta |
| 7,874,489 B2 | 1/2011 | Mercolino |
| 7,875,457 B2 | 1/2011 | Wang et al. |
| 7,885,428 B2 | 2/2011 | Stierman et al. |
| 7,912,653 B1 | 3/2011 | Scher et al. |
| 7,917,298 B1 | 3/2011 | Scher et al. |
| 7,919,018 B2 | 4/2011 | Williams et al. |
| 7,969,281 B2 | 6/2011 | Kofman et al. |
| 8,033,450 B2 | 10/2011 | Stierman et al. |
| 8,088,555 B2 | 1/2012 | True |
| 8,167,212 B2 | 5/2012 | Kofman et al. |
| 8,168,638 B2 | 5/2012 | Oda et al. |
| 8,178,278 B2 | 5/2012 | True et al. |
| 8,220,716 B2 | 7/2012 | Mercolino |
| 8,223,964 B2 | 7/2012 | Stierman et al. |
| 8,247,018 B2 | 8/2012 | Mercolino |
| 2001/0041214 A1 | 11/2001 | Brogger et al. |
| 2002/0084329 A1 | 7/2002 | Kaye et al. |
| 2003/0036201 A1 | 2/2003 | Nelson et al. |
| 2004/0098891 A1 | 5/2004 | Hunt et al. |
| 2004/0169847 A1 | 9/2004 | Dukler |
| 2004/0243022 A1 | 12/2004 | Carney et al. |
| 2005/0276906 A1 | 12/2005 | Metzger |
| 2006/0188402 A1 | 8/2006 | Xie et al. |
| 2007/0012783 A1 | 1/2007 | Mercolino |
| 2008/0045834 A1 | 2/2008 | Uber, III |
| 2008/0118687 A1 | 5/2008 | Burns et al. |
| 2009/0118594 A1 | 5/2009 | Zdeblick |
| 2009/0220789 A1 | 9/2009 | Desimone et al. |
| 2010/0050901 A1 | 3/2010 | Biris et al. |
| 2010/0198141 A1* | 8/2010 | Laitenberger ..... A61M 5/16836 604/65 |
| 2010/0214567 A1 | 8/2010 | Shtatnov |
| 2012/0039809 A1 | 2/2012 | Levinson et al. |
| 2012/0104256 A1 | 5/2012 | Rapoport et al. |
| 2012/0104278 A1 | 5/2012 | Downing et al. |
| 2012/0145924 A1 | 6/2012 | Tinsley |
| 2012/0205449 A1 | 8/2012 | Lewis et al. |

OTHER PUBLICATIONS

Feb. 23, 2015 ISR and WO from PCT/US2014/067435.
"Supplementary European Search Report from EP Application No. EP14865563", dated May 9, 2017.
Gem'innov., "Geminnov Live Colors Customized Microcapsules Brochure", Oct. 12, 2016.
Institute; Of Physics., "Invisible AR codes tackle counterfeit bank notes", Sep. 12, 2012.
Institute of Physics, "Nanoparticle quick response code becomes banknote security feature", Sep. 12, 2012.
Institute of Physics., "Wireless power for the price of a penny", Aug. 10, 2012.
"International Preliminary Report on Patentability from Corresponding PCT App. No. PCT/US2014/067435", dated Jun. 9, 2016.
"International Search Report and Written Opinion from corresponding PCT App. No. PCT/US2014/067435", dated Feb. 23, 2015.
"Mott's Products: Snack & Go Pouches", www.motts.com. Retrieved Oct. 12, 2016.

* cited by examiner

SYSTEM AND METHOD FOR MEDICAL FLUID IDENTIFICATION AND VERIFICATION

CROSS REFERENCE TO RELATED APPLICATIONS

This application is a U.S. national stage filing under 35 U.S.C. § 371 of International Application No. PCT/US2014/067435, filed Nov. 25, 2014, which claims priority to U.S. Provisional Application No. 61/909,109, entitled "System and Method for Medical Fluid Identification and Verification" and filed on Nov. 26, 2013. The disclosures of each of which are incorporated herein by reference in their entirety.

BACKGROUND

Field

The present disclosure relates generally to syringes, injectors, injection systems, and methods of use thereof for injection of contrast, saline, and/or other medical fluids to a patient, and particularly to devices and systems including various agents for identification and verification of the fluid being injected.

Description of Related Art

In many medical procedures, such as drug delivery, it is desirable to inject a fluid into a patient. Likewise, numerous types of contrast media (often referred to simply as contrast) are injected into a patient for many diagnostic and therapeutic procedures, for example, gene therapy, cell and biological agent delivery, and delivery of therapeutic agents generally. For example, contrast media are used in diagnostic procedures such as X-ray procedures (including, for example, angiography, venography, urography), computed tomography (CT) scanning, magnetic resonance imaging (MRI), and ultrasonic imaging. Contrast media are also used during therapeutic procedures, including, for example, angioplasty and other interventional radiological procedures.

In recent years, a number of injector-actuated syringes and powered injectors for pressurized injection of fluids, such as contrast media, have been developed. By way of example, in a typical angiographic procedure, the medical practitioner places a cardiac catheter into a vein or artery. The catheter is connected to either a manual or an automatic contrast injection mechanism. A typical manual contrast injection mechanism includes a syringe in fluid connection with a catheter connection. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, again, such as stopcocks. The operator of the manual contrast injection mechanism controls the syringe and each of the valves to draw saline or contrast into the syringe and to inject the contrast or saline into the patient through the catheter connection. The operator of the syringe may adjust the flow rate and volume of injection by altering the force applied to the plunger of the syringe. Thus, manual sources of fluid pressure and flow used in medical applications, such as syringes and manifolds, typically require operator effort that provides feedback of the fluid pressure/flow generated to the operator. The feedback is desirable, but the operator effort often leads to fatigue. Thus, fluid pressure and flow may vary depending on the operator's strength and technique.

Automatic contrast injection mechanisms typically include a syringe connected to a powered injector having, for example, a powered linear actuator. Typically, an operator enters settings into an electronic control system of the powered injector for a fixed volume of contrast and a fixed rate of injection. In many systems, there is no interactive control between the operator and the powered injector, except to start or stop the injection. A change in flow rate in such systems occurs by stopping the machine and resetting the injection parameters. Automation of angiographic procedures using powered injectors is discussed, for example, in U.S. Pat. Nos. 5,460,609; 5,573,515; and 5,800,397, incorporated herein by reference.

Generally, liquids being injected into a patient, such as X-ray and magnetic resonance contrast are clear pharmaceuticals delivered to a patient during a medical imaging procedure. Such contrasts can be detected by sophisticated imaging systems, but are difficult to detect by eye. Specifically, since air is also clear, it is difficult to distinguish a syringe full of air from a syringe full of a clear fluid and thus there is risk of injecting air instead of contrast or other drug into a patient, which can be harmful or fatal. In addition, it is difficult to determine if an extravasation of the contrast is occurring. In addition, different contrasts have different properties, which make it difficult for a single or standard detector system to measure a property of the contrast, for example its presence or its concentration. Further, it may be desirable to trace a medical fluid comprising an active medicament in vivo during or after an injection procedure On the other hand, it is desirable that the contrast be clear to enable the user to check for impurities or small bubbles before injecting the fluid into the patient. These impurities could be solid particles or improper chemicals with an identifiable color. For the visualization of particles, the contrast only needs to be transparent, but may be lightly colored. For example, if X-ray contrast is stored improperly, free iodine can be released, causing the contrast to have a yellow tint. To best detect this tint, it is desirable that the contrast be clear or, at least initially, un-tinted.

Therefore, there is a need for a syringe, injector, or injection system capable of identifying and validating the solution prior to, during, or after an injection. For example, the validation system should recognize air bubbles in the solution prior to injection, as well as, contrast agents that have been improperly stored, mixed, or used. Further, it may be desirable to follow and determine specific properties or events during or after an injection procedure. The injector or system may include various fluid additives, labels, barcodes, sensors, detectors, or cameras, for identifying and validating the contrast prior to injection. The medical fluids, syringes, injectors, and systems set forth in the present disclosure are configured to address some or all of the above-identified problems.

SUMMARY

According to one aspect, the present disclosure provides a system for injection of a fluid to a patient is provided. The system includes a fluid to be injected, the fluid having at least one active compound and at least one tracer compound; an injector configured to deliver the fluid to the patient through a fluid path set; at least one sensor coupled to at least one of syringe fluid container associated with the injector, the fluid path set, the injector, and the patient, wherein the at least one sensor is configured to measure at least one property of the at least one tracer compound in the fluid. The system further includes a feedback path configured to adjust injection parameters of the injector based on a measurement from the sensor. In various embodiments, the feedback path may be a servo control feedback path in communication with an operating system of the injector and capable of adjusting the one or more injection parameters of the injector in a real time manner based on the measurement from the at least one sensor. In certain embodiment, the at least one active compound and the at least one tracer compound may be the same compound. In certain embodiments, the at least one tracer compound may comprise at least one nanoparticle, at least one dissolved molecule, or at least one microbubble.

According to another aspect, the present disclosure provides a method for measuring a property of an injected fluid in a vascular system. The methods may comprise injecting a fluid comprising at least one active compound and at least one nanoparticle tracer compound into a vascular system of a patient, associating at least one sensor with a tissue section of the patient, irradiating the tissue section with electromagnetic radiation having at least one first wavelength from an electromagnetic radiation source, measuring at least one of the presence of electromagnetic radiation having the at least one second wavelength, the absence of electromagnetic radiation having the at least one second wavelength, and the location of the electromagnetic radiation having the at least one second wavelength, and changing at least one injection parameter of the injector in a real time manner based on the results of the measuring step. The at least one sensor may comprise an electromagnetic radiation source for emitting electromagnetic radiation having at least one first wavelength and an electromagnetic radiation detector for detecting electromagnetic radiation having the at least one second wavelength. In certain embodiments, the at least one nanoparticle tracer compound may comprise at least one up-converting fluorescent nanocrystal and the at least one active compound may comprise at least one contrast agent. In other embodiments, the at least one active compound may be the at least one nanoparticle tracer compound. The method may further comprise the step of determining from the measuring of the electromagnetic radiation having the at least one second wavelength one or more of a flow rate of the at least one active compound in the vascular system, the direction of flow of the at least one active compound in the vascular system, the presence of air in the vascular system, the presence of extravasation of the at least one active compound, a volume rate of the at least one active compound in the vascular system, a bolus concentration of the injected fluid, a bolus sharpness of the injected fluid, a value for an estimated glomerular filtration rate, volume of distribution, circulation time, cardiac output, delay time to organs of interest and other physiologic parameters, or combinations of any thereof.

According to another aspect, the present disclosure provides a system for injection of a fluid to a patient. The system may comprise a fluid comprising at least one up-converting fluorescent nanocrystal, an injector configured to deliver the fluid to a patient through a fluid path set, at least one sensor coupled to a tissue section of the patient wherein the at least one sensor is configured to measure at least one property of the fluorescent nanocrystal in the patient, and a feedback path configured to adjust at least one injection parameter of the injector based on at least one measurement from the at least one sensor. In specific embodiments the tissue section of the patient may be a dermal tissue section of the patient. In various embodiments, the fluid may further comprise a contrast agent. In certain embodiments, the at least one property of the fluorescent nanocrystal in the patient may be selected from the group consisting of a concentration of the fluorescent nanocrystal at a site within the patient near the tissue section, a location of the fluorescent nanocrystal within a vascular system of the patient near the tissue section, an extravasation of the fluorescent nanocrystal outside the vascular system of the patient near the tissue section, a flow rate or flow direction of the fluorescent nanocrystal in the vascular system of the patient near the tissue section, a bolus sharpness of the fluid in the vascular system of the patient near the tissue section, a value for an estimated glomerular filtration rate of the patient, and combinations of any thereof. In various embodiments, the feedback path may be a servo control feedback path in communication with an operating system of the injector and capable of adjusting the one or more injection parameters of the injector in a real time manner based on the measurement from the at least one sensor.

According to a further aspect, a system for injection of a fluid to a patient is provided. The system includes a syringe including a syringe barrel and having at least one tracer compound attached to or integrally formed with the barrel; an injector configured to receive the syringe and to deliver the fluid contained within the syringe to the patient through a fluid path set; and a sensor coupled to the injector or syringe configured to detect and to obtain data from the at least one tracer compound.

According to a further aspect, a system for injection of a fluid to a patient includes a fluid container holding the fluid to be injected; a pump for drawing fluid from the container into a temporary fluid bag; and a rotation mechanism for inverting the temporary fluid bag. The system is configured such that, upon inverting the fluid bag, the pump action is reversed to expel fluid from the temporary fluid bag to a patient through a patient port. In certain configurations, at least one tracer compound is attached to or integrally formed with the fluid container. The at least one tracer compound may include information about the container, the fluid contained within the container, a property of the fluid after injection, or a combination thereof.

BRIEF DESCRIPTION OF THE DRAWINGS

Some of the advantages and features of the preferred embodiments of the disclosure have been summarized hereinabove. These embodiments, along with other potential embodiments of the device, will become apparent to those skilled in the art when referencing the following drawings in conjunction with the detailed descriptions as they relate to the figures.

DESCRIPTION

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. It is to be understood, however, that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

Figure 1:
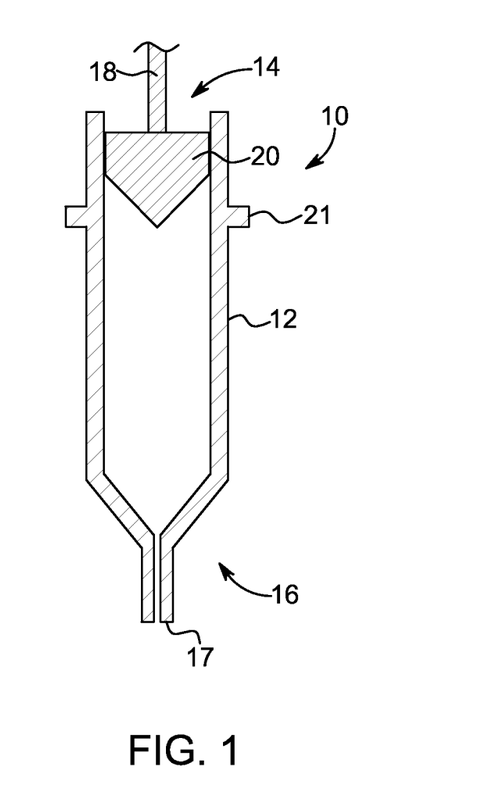
FIG. 1 is a schematic drawing of a syringe, according to one embodiment.

Provided herein are syringes, injectors, systems, and methods for injection of medical fluid to a patient. According to the various embodiments described herein, the medical fluid may comprise at least one tracer compound. The syringes, injectors, and fluid delivery systems are configured with various features to improve validation, identification and tracking of the medical fluid prior to, during, and after injection into a patient. With reference to FIG. 1, fluid may be injected by a pump or a syringe, such as a disposable syringe 10. Such syringes generally include a cylindrical barrel 12, an open proximal end 14, and a distal end 16 terminating in a nozzle 17, for example having a luer connector configured to provide fluid communication with a needle cannula or catheter. A piston rod 18 advances a plunger 20 through the barrel 12 from the proximal end 14 toward the distal end 16, thereby expelling fluid from the syringe 10 through the nozzle 17, luer connector, needle cannula, and/or catheter. The nozzle 17 or luer connector may be placed in fluid communication with a fluid path set, for example, a catheter for delivery of the fluid to a patient. A syringe 10 having a nozzle 17 or luer connector may be manually operated or may be connected to a powered injector for automated injection at a controlled flow rate. In the latter case, the syringe 10 may include structures 21 for reversible attachment with a corresponding attachment mechanism of the powered injector. Alternatively, for syringes 10 having a needle cannula, the fluid may injected directly to the patient through the needle.

Figure 2:
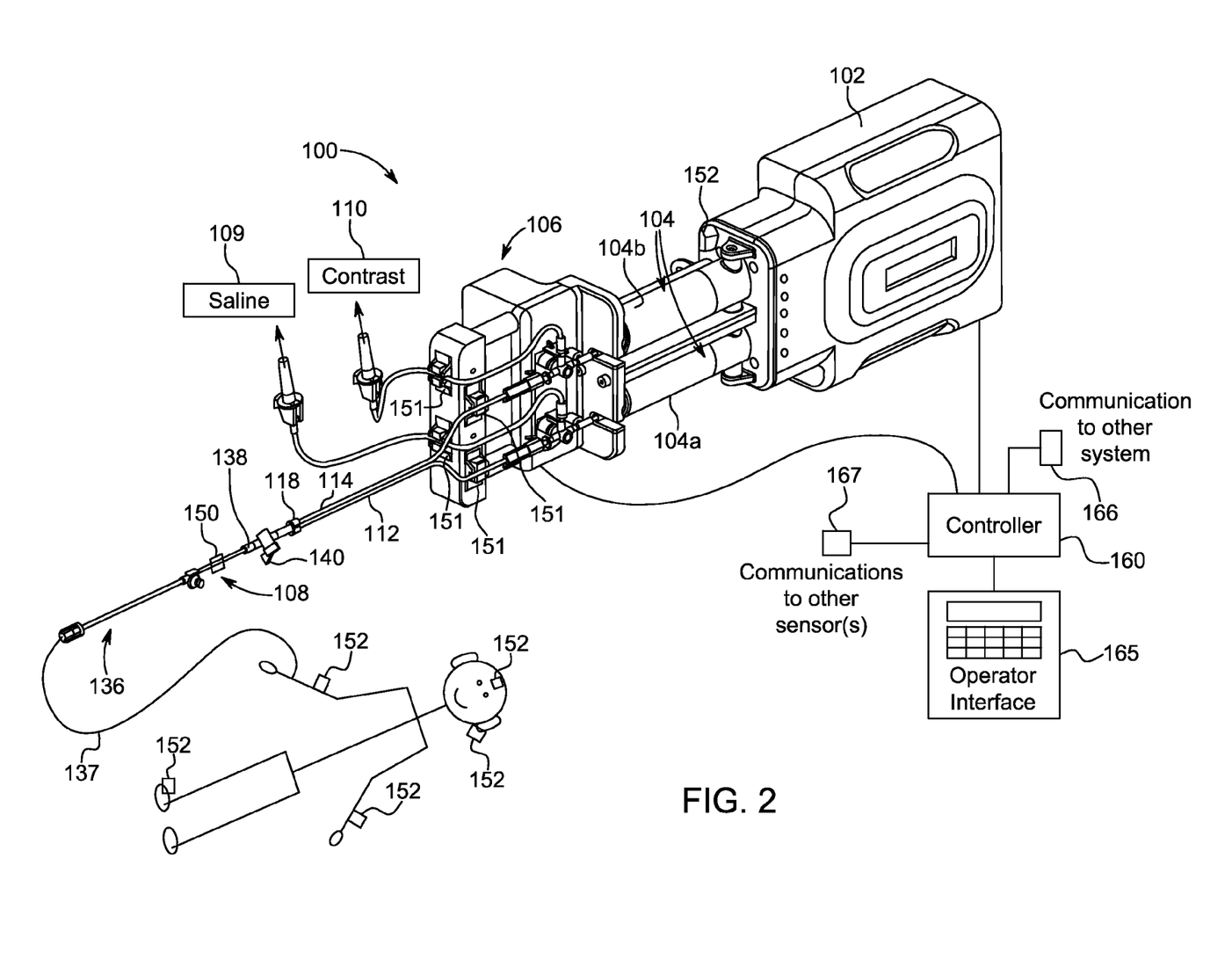
FIG. 2 is a perspective view of a fluid delivery system including a powered injector, according to an embodiment.

With reference to FIG. 2, one non-limiting embodiment of a fluid delivery system 100 having a powered fluid injector 102 adapted to accept and actuate a plurality of syringes, such as the two syringes 104, is illustrated. The syringes 104 are fluidly connected to two (2) fluid reservoirs, such as a source of saline 109 and a source of contrast media 110 or other medical fluid, or any two desired medical fluids. The fluid injector 102 may include at least two syringes 104, such as a dual-syringe injector, wherein the two (2) fluid delivery syringes 104a, 104b are oriented in a side-by-side or other relationship, and which are separately actuated by respective piston elements associated with the fluid injector 102. A fluid path set 108 may be interfaced with the syringes 104 associated with the fluid injector 102 of the fluid delivery system 100. In certain embodiments, the fluid injector 102 may include a fluid control module 106 that is generally adapted to support and interface the syringes 104 with the fluid path set 108; the fluid control module 106 may have various control valves and like elements to control the fluid flow through the fluid path set 108 connected to the syringes 104. A fluid delivery system 100 may further include a controller 160 which may interface with one or more of the fluid injector 102, the fluid control module 106, an operator interface 165, a communication port 166 configured to communicate to at least one other system, for example a hospital information system or an informatics platform such as the Certegra product, commercially available from Bayer Medical Care, Indianola, Pa., or a sensor communications port 167 which may be configured to interface with the one or more sensors, for example by a wired or wireless set up. One embodiment of a suitable multi-syringe fluid injector for use with the system disclosed herein is described in U.S. patent application Ser. No. 13/386,765, which published as U.S. Patent Application Publication No. 2012/0123257, and is assigned to the assignee of the present application, the disclosure of which is incorporated herein by reference in its entirety. Other relevant multi-fluid delivery systems that may be suited for use with the present system are disclosed in U.S. patent application Ser. No. 10/159,592 (published as U.S. 2004/0064041), and U.S. patent application Ser. No. 10/722,370 (published as U.S. 2005/0113754), each of which are assigned to the assignee of the present application and the disclosures of which are incorporated herein by reference in their entireties.

The fluid path set 108 may have single and multi-use disposable sections. The fluid path set 108 includes a first input line 112 in selective fluid communication with a first syringe 104a, a second input line 114 in selective fluid communication with a second syringe 104b, a downstream Y-connector 118 joining the first and second input lines 112, 114, and a catheter connector conduit 136. The catheter connector conduit 136 may be a disposable tubing section that connects the fluid path set 108 to a catheter 137 that is inserted within a patient for supplying the fluids from the saline or flushing fluid source 109 and the contrast media source 110, or other medical fluid source to the patient. Desirably, the catheter connector conduit 136 is removably connected by a suitable connector 138 to a stopcock valve 140 that is provided between the Y-connector 118 and the catheter connector conduit 136. The stopcock valve 140 may form a break point between reusable multi-use components of the fluid path set 108 and the disposable single-use catheter connector conduit 136 in one embodiment. This configuration permits a user to isolate the reusable upstream components of the fluid path set 108 so that, when the stopcock valve 140 is in a closed position, a user can remove and replace the catheter connector conduit 136, and so that the multi-patient section of the fluid delivery system 100 can be used with one or more additional patients. In certain embodiments, the fluid path set may further include one or more check valves to prevent backflow of contaminated fluid from the single-use portion of the fluid path to the multi-use portion of the fluid path. The stopcock 140 is merely an exemplary structure for isolating the upstream components from the catheter connector conduit 136 and may be replaced by any suitable aseptic connector structure. According to certain embodiments, the stopcock 140 may present the advantage of being manually actuated. In certain embodiments, at least one of at least one active compound and at least one tracer compound, as described herein, may be contained in at least one syringe or at least one multi-dose container and the injector may be configured to receive the at least one syringe or the at least one multi-dose container and deliver the fluid in the at least one syringe or the at least one multi-dose container to the patient through fluid path set, such as 108.

Having generally described the structure of syringes, injectors, and fluid delivery systems for delivering at least one medical fluid to a patient, various embodiments including features for improved verification and identification of fluids prior to injection and determination of properties of the fluid during or after the injection will now be discussed. In one non-limiting embodiment, the fluid or fluids to be injected by the syringes, injectors, and systems may be provided with increased visibility, for example by being colored or having various fluorescent properties, to reduce the possibility for operator error during the injection process. Increasing the visibility of the fluid agent helps the operator to more easily identify and prevent leakage of the fluid from the injector or fluid path set, or during injection, for example, extravasation (e.g., leakage of fluids into patient tissue). Leaks within tubing, containers, or valves are more easily identified and corrected when the fluid is visible to the eye. Other sensors suitable for use with various embodiments of the present system include photocells, photocell patches, cameras or other sensors configured to sense and/or quantify one or more specific wavelengths of electromagnetic radiation, for example visible or infrared electromagnetic radiation, and transmit data related to the presence, absence or intensity of the electromagnetic radiation at the one or more specific wavelengths. In certain embodiments, at least one sensor may include a filter to affect it's spectral response.

Figure 3:
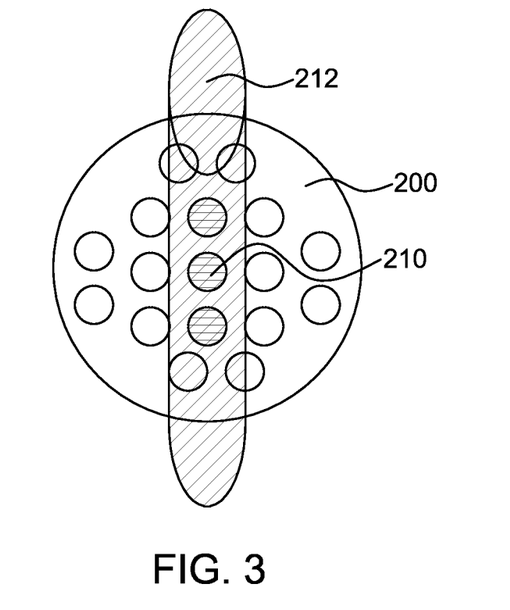
FIG. 3 is a schematic drawing of a detector for extravasation of fluid, according to an embodiment.

In addition to manual checking by a medical technician or system operators, electronic detectors, such as at least one sensor, may also be used to identify leaking fluid. For example, with reference to FIG. 3, a detector 200 may be configured to identify fluid 210 within a vessel 212, such as a fluid path or a vein, artery or tissue of a patient, by measuring the intensity of absorbed light within the visible spectrum or by irradiating vessel 212, with electromagnetic radiation having at least one first wavelength and detecting the presence of electromagnetic radiation having at least one second wavelength. If fluid 210 is identified in a location not consistent with the location of the vessel 212, it may indicate fluid leakage. For example, in the case of an extravasation event, the at least one sensor may indicate that the fluid is located outside of the intended section of the patient vasculature and is, instead, leaking into the surrounding tissue adjacent the injection site, as a result, the system could alert the operator to an extravasation event or, alternatively, automatically shut down the injection procedure until the extravasation can be remedied. Similarly, if the intensity of absorbance continues to increase, it would tend to indicate that leaking fluid is collecting in and around the detector 200.

Including at least one tracer compound, for example pigments, visible particles, and/or fluorescent compounds or compositions in a medical fluid may also be beneficial for use with injectors that mix two or more fluid components prior to injection. Particularly, one component, such as contrast media, may be provided with at least one tracer compound, for example a pigment. A second component, such as saline, may be clear. An operator can visually determine as the mixed fluid passing through the fluid path set, tubing, or catheter whether the mixing process is being carried out successfully. For example, it would also be apparent if the two solutions did not mix well, for example by observing the intensity or consistency/uniformity of the color of the mixture, which may alert an operator to an error or mistake. For example, fluids that fail to mix fully may indicate that the fluids have incorrect viscosity, concentration, or are simply not meant to be mixed together. An operator who recognizes that fluids fail to mix may prevent the fluid from being injected to the patient by, for example, closing a valve on the fluid path set or turning off the injector. Furthermore, in the case of contrast media and similar solutions used in medical imaging applications, using solutions that are visible to the human eye allows the operator to more easily determine the concentration of contrast agent relative to clear saline. Therefore, by visually quantifying the contrast concentration, the operator may be able to better understand why an angiographic image appears to be bright or washed out. Specifically, the operator can simply look at the color of the solution being injected to the patient to determine the concentration of contrast media versus saline. Similarly, the operator may be better able to understand characteristics of the mixed fluid including viscosity, flow rate, and pressure implications. Density exchange awareness is also more easily realized.

According to one embodiment, one method to increase visibility of a fluid is by including at least one tracer compound, such as a at least one nanoparticle, at least one microbubble, or at least one dissolved molecule, such as a fluorescent compound, a pigment, or a dye, within the fluid to be injected. For example, the at least one tracer compound may be added to fluid within a prefilled syringe or cartridge, such as syringes or cartridges used by the powered injector depicted in FIG. 2. The added at least one tracer compound, such as a fluorescent compound, pigment or dye is intended to make the fluid visible to the human eye. According to various embodiments, the at least one tracer compound could be at least one atom, molecule, particle, microbubble, nanocrystal, or combinations thereof, which, when dissolved in or suspended in solution, reflects, refracts, transmits, absorbs and/or generates light (such as by fluorescence or phosphorescence), for example within the visible portion or other portion of the electromagnetic spectrum for sensing by a sensor or by the human eye. Alternatively, the at least one tracer compound may generate light having a wavelength that can be detected by some other sensor, such as a camera or a photocell, such as a photocell patch. The at least one tracer compound should be inert, non-reactive with the reservoir container, tubing of the fluid path set, and/or the patient, and/or, to the extent possible, be biocompatible and readily excreted or metabolized by the renal, liver or other excretory system.

Advantageously, the fluid including the at least one tracer compound and at least one active compound may be relatively dilute, meaning that the fluid including the at least one tracer may be essentially transparent. Accordingly, an operator can readily see any air bubbles, particles and/or other contaminants within the solution. The color of the solution, if any, should also be easily discernible by an operator in a well lit room.

Alternatively, chemical compounds and compositions having optical absorption and fluorescence or phosphorescent properties in response to absorbed electromagnetic radiation are also within the scope of the present disclosure. A benefit of fluorescence is that the output signal is commonly proportionally related to the input radiation intensity and has an output radiation at a single or limited number of defined wavelengths. As a result of this proportional relationship, an intense input can provide a discernible output even when the concentration on the tracer in the solution is dilute, for example at the trace or microdose level. In one embodiment, the organic compound Fluorescein is an example of a dye having such absorbent and fluorescent properties. The input or excitation radiation of a dye, compound, molecule, or particle may also vary over time, which facilitates detection and recognition by the operator or an automated detector of the output signal, as compared to the background or other interfering signals. For example, by pulsing the excitation radiation, the fluorescent footprint of the compound will also pulse, thereby differentiating it from other sources of electromagnetic radiation.

In addition to being used for validation of fluid and/or the fluid path set prior to injection, fluids containing tracer compounds may also be used for identification of the medical solution to be injected and for following or determining certain properties of the fluid during and after injection into a patient. For example, specific types of contrast media could always be provided in a specific color. Thus, operators would begin to look for a specific color before beginning an injection. Accordingly, the possibility that an operator could accidently inject incorrect contrast or medication may be effectively reduced. In certain embodiments, the tracer compound may be the same for all contrast media. Thus, the presence of the tracer compound may be effective for distinguishing between contrast and other medical solutions, such as solutions comprising non-contrast medications; however this embodiment would not be effective for distinguishing between different types of contrast agents. Alternatively, the tracer properties could be varied in a controlled way to help authenticate the contrast media (e.g., determine the source and authenticity) and/or its properties. Additionally, multiple tracer compounds that absorb and/or emit as different specific wavelengths could be used in various combinations to achieve multiple coding possibilities.

According to specific embodiments, the present disclosure provides a system for injection of a fluid into a patient. The system may comprise a fluid having at least one active compound and at least one tracer compound, such as any of the tracer compounds described herein, an injector configured to deliver the fluid to a patient through a fluid path set, at least one sensor coupled to at least one of a fluid container associated with the injector, the fluid path set, the injector, and the patient, wherein the at least one sensor is configured to measure at least one property of the at least one tracer in the fluid, and a feedback path configured to adjust at least one injection parameter of the injector based on at least one measurement from the at least one sensor. Such adjustments may take place before or during the injection procedure. In specific embodiments, the feedback path may be a servo controlled feedback path configured to adjust the at least one injection parameter of the injector in a real time manner. The at least one tracer compound may comprise at least one nanoparticle, at least one dissolved molecule, or at least one microbubble.

According to certain embodiments, the at least one tracer compound could comprise a molecule or particle, such as a nanoparticle, that is capable of absorbing electromagnetic radiation having at least one first wavelength and emitting electromagnetic radiation having at least one second wavelength, for example within the visible region of the spectrum. An example of a tracer compound may be a nanoparticle capable of such output, such as sunstone up-converting nanocrystals, available from Sigma Aldrich and manufactured by IMS-Intelligent Materials Solutions Inc., Princeton, N.J. See http://www.sigmaaldrich.com/technical-documents/articles/biology/upconverting-ucp-nanocrystals.html; and http://sunstones.com/. Sunstone up-converting nanocrystals absorb two photons of infrared radiation and emit a single photon in the visible region. Thus, according to certain embodiments, the at least one tracer compound may be at least one up-converting fluorescent nanocrystal comprising a fluorophore compound that absorbs two or more low-energy photons having at least one first wavelength, for example in the infrared region of the electromagnetic spectrum and emits at least one higher energy photon having at least one second wavelength in a visible region of the electromagnetic spectrum. According to a specific embodiment, the at least one second wavelength may be in the green or blue region of the visible region and the higher energy photon may penetrate through at least a portion of a tissue of a patient into whom the fluid comprising the nanoparticle has been injected. Thus, the higher energy photon may be observed or sensed by a sensor placed on a tissue section of the patient adjacent to or remote from the injection site.

Sunstone particles have an excellent medical safety profile. The particles are generally inert, with no known safety issues. Furthermore according to various embodiments, trace, nanomolar, or micromolar quantities of particles can be used in the fluid, while still allowing accurate detection and quantification. The nanoparticles particles are typically of a size and/or shape below the renal threshold that allows for rapid renal excretion, for example by filtration by the glomeruli in the kidneys and excretion, proportional to renal excretion of contrast. Thus, the Sunstone particles will not remain in a patient's body for an extended period of time. Alternatively, a tracer compound, such as a fluorescent compound or other nanoparticle, capable of absorbing electromagnetic radiation as a first wavelength and emitting by fluorescence, electromagnetic radiation having a longer wavelength could also be utilized. According to this embodiment, the at least one tracer compound may be at least one down-converting nanoparticle or fluorophore.

A further benefit of a nanocrystal tracer compound or other fluorescent compound is that nanocrystals and fluorophores absorb a specific wavelength of light and can be designed to emit at a specific higher or lower wavelength as determined by the specific fluorescent compounds, such as those within the nanocrystals. The emitted wavelength can be detected manually, that is visually by an operator, or detected using an electronic sensor. In either case, because of the specificity and controllability of emission wavelength, interference from background can be significantly reduced or eliminated. Individuals or sensors can be built to look for a specific color or wavelength of emitted light and to ignore light of different colors/wavelengths from other sources. Further, the at least one sensor may also be configured with an electromagnetic radiation source for emitting electromagnetic radiation having the at least one first wavelength, along with an electromagnetic radiation detector for detecting the electromagnetic radiation having the at least one second wavelength.

Another benefit of using up-converting nanocrystal particles, such as Sunstone, or other tracer compounds described herein, is that the amount of tracer compounds added to the contrast can be so low that the added particles are considered to be trace constituents in an injected fluid. For example, the U.S. Food and Drug Administration's ("FDA") definition of a "trace" constituent for dosing is less or equal than 10 ppm, whereas a "microdose" is defined as up to 100 μg per dose or not more than 500 μg per subject if multiple doses are administered. While the concentration of the tracer compound of various embodiments of the present disclosure are not limited to these or any concentrations, it may be commercially desirable to be at or below one or both of these levels. As described above, the fluid and the output or absorbance of the tracer compound may be visible to the human eye, allowing an operator to examine the solution and to modify the injection if any problems are identified. In further non-limiting embodiments, syringes, injectors, or fluid injection systems may be provided with various sensors and detectors for automatically identifying and validating medical fluids prior to or during injection.

With reference again to FIG. 2, the powered injector may be provided with such at least one sensor or detector 150. For example, in one embodiment the at least one sensor or detector 150 may be positioned in the fluid path set 108 distal to the y-connector 118. In this way, the at least one sensor or detector 150 may measure the quality of the mixed fluid prior to injection. According to various embodiments, the at least one sensor or detector 150 may include sensing means for identifying the fluid containing the specific tracer compounds being identified, for example an electromagnetic radiation source that emits radiation having at least the first wavelength and a sensor for detecting the specific wavelength(s) of light emitted by the at least one tracer compound. In addition or alternatively, at least one sensor or detector 151 may be positioned along other elements of the fluid path to assess the fluid or confirm presence of the correct fluid, for example by detecting the tracer compound or noting the absence of the tracer compound in the fluid. Similarly, in the case of tracer particles that fluoresce outside the visible spectrum or which are activated by one or more wavelength of light outside the visible spectrum, the at least one sensor or detector 150, 151 may also have an energy source, such as an infrared emitting energy source or red laser or other emitter of electromagnetic radiation at an excitation wavelength that causes the tracer compound to fluoresce, to irradiate the tracer compound identify the tracer particles within the solution based on the emitted radiation. In certain embodiments, the at least one sensor may be at least one of a photocell or photo detector patch (such as 200 shown in FIG. 3) or a camera. The sensing means may measure one or more of the following characteristics of the solution, including, but not limited to color shade of the solution, light refraction, tracer content or concentration, pH level, radioactive content, flow rate of the fluid, bolus sharpness, and other properties of the tracer compound or other drug additives.

In certain embodiments, the at least one sensor may be coupled to a tissue section of a patient, such as, for example a dermal tissue section of a patient. In other embodiments, the at least one sensor may be associated with an internal tissue section of the patient, such as where the at least one sensor is on an endoscope, catheter or other medical device inserted within the patient. According to various embodiments, the at least one sensor may be configured to measure in vivo at least one property of the injection fluid such as, for example a concentration of the tracer compound at a site within the patient near the tissue section, a location of the tracer compound within a vascular system of the patient near the tissue section, an extravasation of the tracer compound outside of the vascular system of the patient near the tissue section, or combinations of any thereof.

In certain embodiments, the sensing means may be connected within an electronic feedback path, such as a servo feedback path. The feedback path may include a controller configured to receive data from the at least one sensor and to adjust at least one injection parameter of the injector based on the received data from the at least one measurement. In certain embodiments, the controller may be configured to receive input from the operator. For example, the controller may be configured to open or close various valves, increase injection flow rate, or any combination thereof for the purpose of improving the quality of the injected fluid. The controller could also be configured to stop injection or alert a user if certain problems, such as, air or bubbles in the solution, incorrect concentration, or pH outside of acceptable levels, are identified. Thus, the sensing means is a real time sensor capable of updating the solution concentration in real time. In certain embodiments, the at least one injection parameter of the injector that is adjusted in response to the sensor date may include decreasing an injection rate, increasing an injection rate, stopping an injection, changing an injection stop time, or changing a concentration of the at least one active compound in the fluid.

In a further non-limiting embodiment, illustrated in FIG. 2, the sensing means, such as the at least one sensor, 152 may be positioned and configured to detect and measure properties of the tracer compounds, for example, concentration and location, directly within the blood vessels, vasculature) or tissue of a patient. For example, the sensing means may be placed on a patient's skin and may be capable of measuring tracer concentration and/or location within a given portion of skin tissue with some depth sensitivity that may depend on the type of tracer compound, wavelength(s) of absorbed and/or emitted radiation, and the energies involved. In an example embodiment, the at least one sensor may be coupled to a tissue section, for example a dermal tissue section of the patient, over or near the injection site. In another embodiment, the at least one sensor may be placed as a tissue section located away from the injection site but close to a region of interest in which one or more property of the injected fluid is to be measured. According to certain embodiments, the at least one sensor may be configured to measure the exact time of bolus arrival in the measured region. In other embodiments, the at least one sensor may be configured to measure bolus concentration or sharpness by measuring tracer concentration in the vasculature of the patient. In other embodiments, the at least one sensor may be placed at a site remote from the injection site, for example on the arm opposite the arm where the injection occurs, such that the bolus shape and/or timing may be assessed after having passed through the central circulation system. In other embodiments, the at least one sensor may be placed, for example, on a patient's ear or forehead to assess the bolus for imaging of the head. In another embodiment, the sensor may be placed on the patient's leg, foot, or toe, for example for a run-off imaging study. In other embodiments, the at least one sensor may be associated with an endoscope or a catheter for assessing properties of the injected fluid within the patient. As described above, the sensing means may be coupled to a feedback path so that data provided by the at least on sensor may be transmitted to the controller and at least one property of the injection, for example the flow rate or solution concentration can be automatically modified based on measurements taken by the sensing means when the operator is alerted or the controller determines that a modification is necessary. The at least one sensor may also be configured to transmit data requiring the controller to stop the injection, for example if an extravasation occurs. In certain embodiments, the feedback path in concert with a computer operated controller can act very quickly, on the order of seconds or fractions thereof. The feedback path may also be configured for longer term feedback, such as minutes or hours, for example in therapeutic cases. The feedback path may also interface with one or more other associated equipment, such as an imaging system, to alert the system to the existence of the conditions (e.g., when enough contrast concentration is present) sufficient to commence an imaging sequence, or for example to not start, to stop, or to abort an imaging sequence if an extravasation occurs. This feedback path may be used so that the imager, for example, a CT scanner, is not required to irradiate the patient while checking for the occurrence of a sufficient concentration of contrast. The at least one sensor sensing the amount of the tracer compound may be used to determine when the contrast level is sufficient for initiating the imaging scan.

In certain embodiments, the at least one active compound may comprise a contrast agent and the at least one tracer compound may comprise at least on compound or nanoparticle capable of absorbing electromagnetic radiation having at least one first wavelength and emitting electromagnetic radiation having at least a second wavelength. According to other embodiments, the at least one active compound and the at least one tracer compound may be the same compound, for example, both the active compound and the tracer compound may be an up-converting nanocrystal or other tracer compound described herein. According to systems where the at least one active compound and the at least one tracer compound are the same, for example, up-converting nanocrystals, the system may be configured to measure an estimated glomerular filtration rate for the patient.

After administration of the at least one tracer, such as the nanocrystals or other fluorescent species, the electromagnetic radiation may be measured to determine the peak after distribution into the fluid compartment and then at one or several time points or continuously to determine the decrease in electromagnetic radiation over time due to metabolism and/or excretion of the tracer. This rate of decrease in the intensity of the electromagnetic radiation may be used to determine the estimated Glomerular Filtration Rate. The total volume of distribution of the tracer may be determined from the decrease (i.e., dilution) of the input bolus intensity summed over time to the peak intensity after distribution into the fluid depatrement. According to one embodiment a fluorescent tracer, such as a fluorescent compound or nanoparticle, may be used to assess the estimated Glomerular Filtration Rate ("eGFR") for a patient to determine the patient's suitability to receive a contrast injection for imaging and/or to adjust the amount of contrast that they receive based on the eGFR. In this example embodiment, a solution with a tracer, with or without any additional active compounds, is injected into the patient and after a time for the tracer to distribute uniformly thought the blood, the concentration of the tracer in a section of tissue is measured. The concentration and time are recorded. A second or additional measurements are taken over an extended time period, and provided that the tracer is of a size to be excreted by the kidneys, the decay in concentration of the tracer in the blood over time can be used to estimate the glomerular filtration rate. Multiple measurements may be done to more accurately estimate the eGFR. In an example embodiment, the final measurement may be done just prior to the active compound injection and imaging procedure using a sensor associated with an injector. The previous measurement(s) and the time of their measurement(s) are entered into the injector for the computation of an eGFR which is communicated to the user or doctor and is used by them in their decisions about volumes and flow rates of active compound to administer. This is a feedback path which includes the operator in the loop. Alternatively the injector can compare the eGFR with data in its internal programs and databases and adjust the parameters appropriately, optionally with the final approval and check by the operator.

According to certain embodiments, of the present disclosure, a system for injection of a fluid into a patient is provided. The system may comprise a fluid comprising at least one up-converting fluorescent nanocrystal, an injector configured to deliver the fluid to a patient through a fluid path set, at least one sensor coupled to a tissue section of the patient, and a feedback path configured to adjust at least one injection parameter of the injector based on at least one measurement from the at least one sensor. The at least one sensor may be configured to measure at least one property of the fluorescent nanocrystal in the fluid selected from the concentration of the fluorescent nanocrystal at a site within the patient near the tissue section, a location of the fluorescent nanocrystal within the vascular system of the patient near the tissue section, an extravasation of the fluorescent nanocrystal outside the vascular system of the patient near the tissue section, a flow rate or flow direction of the fluorescent nanocrystal in the vascular system of the patient near the tissue section, a bolus sharpness of the fluorescent nanocrystal in the vascular system of the patient near the tissue section, a value for an estimated glomerular filtration rate, and combinations of any thereof. In specific embodiments, the feedback path may be a servo control feedback path configured to adjust the injection parameter(s) in a real time manner. The at least one injection parameter may be selected from decreasing an injection rate, increasing an injection rate, stopping an injection, changing an injection stop time and changing a concentration of at least one active compound in the fluid.

According to other embodiments of the present disclosure, a method for measuring a property of an injected fluid in a vascular system is presented. The method comprises injecting a fluid comprising at least one active compound and at least one tracer compound, such as a nanoparticle or fluorophore, for example an up-converting nanocrystal, into a vascular system of a patient; associating at least one sensor with a tissue section of the patient, wherein the at least one sensor includes an electromagnetic radiation source for emitting electromagnetic radiation having at least one first wavelength and an electromagnetic radiation detector for detecting electromagnetic radiation having at least one second wavelength; irradiating the tissue section with electromagnetic radiation having at least one first wavelength from the electromagnetic radiation source; measuring at least one of the presence of electromagnetic radiation having the at least one second wavelength, the absence of electromagnetic radiation having the at least one second wavelength, and the location of the electromagnetic radiation having the at least one second wavelength using the electromagnetic radiation detector on the at least one sensor; and changing at least one injection parameter of the injector based on the results of the measuring step. In certain embodiments, the changing the at least one injection parameter may be performed in a real time manner based on the measuring step results. In various embodiments, the electromagnetic radiation source may be separate from the at least one sensor and the electromagnetic radiation detector. According to various embodiments, the tissue section of the patient may be adjacent to a portion of the vascular system where the fluid from the injector is expected to flow. For example, in one embodiment, the tissue section may be adjacent to the injection site and in another embodiment, the tissue section may be remote from the injection site and in certain embodiment, the tissue section may be in an interior lumen within the patient. In certain embodiments where the tissue section is in close proximity to a region of interest in the body which can be remote from the injection site, the injection time and the time for the active compound and tracer to reach the region of interest may be determined and used to trigger a procedure, such as an imaging procedure of the region of interest.

In various embodiments the method may further comprise determining from the measuring of the electromagnetic radiation having the at least one second wavelength one or more of a flow rate of the at least one active compound in the vasculature system, a direction of flow of the at least one active compound in the vascular system, the presence of air in the vascular system, the presence of an extravasation of the at least one active compound, a volume rate of the at least one active compound in the vascular system, a bolus concentration of the injected fluid, a bolus sharpness of the injected fluid, a value for an estimated glomerular filtration rate, or combinations of any thereof.

Similarly, other embodiments may include active agents selected from injected therapeutic agents or drugs and the at least one sensor may be configured for non-invasive measurement of drug compounds within a patient's arteries or veins. For example, various metabolites may be tagged with at least one tracer compound, as described herein, and measured to monitor drug levels during continuous drug delivery procedures. Similarly, a "smart" insulin pump may be provided which continuously measures actual blood sugar concentration. Insulin level may be modified based on the blood sugar level measured by the sensor.

Figure 4:
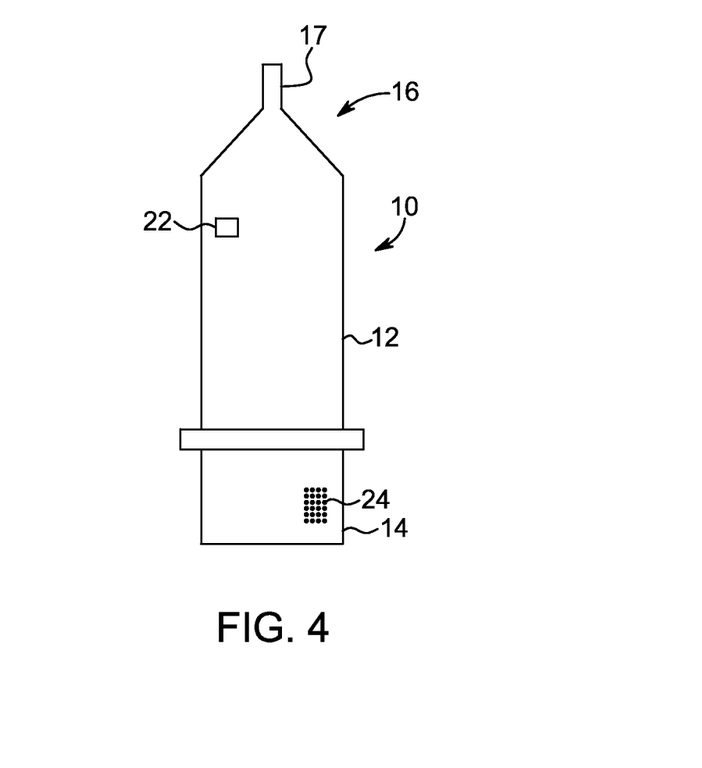
FIG. 4 is a schematic drawing of a syringe having a microdot pattern and QR code included thereon, according to an embodiment.

According to another aspect, the syringe or injector structure itself may be tagged with various tracers or markers for improved identification and verification of fluid contents prior to injection. With reference to FIG. 4, in one non-limiting embodiment, a syringe barrel 12 is provided with a code or tracer compound, such as a three-dimensional bar code, known as a Quick Reference (QR) code 22. The code 22 may be a standard visible QR code, as is known in the art. Alternatively, the QR code 22 may be an invisible indicia printed with florescent or up-converting ink. The ink may become visible after being irradiated by a source of electromagnetic radiation of the appropriate wavelength, such as a laser. For example, the ink may work according to the same up-conversion process used by the Sunstone particles, described herein.

In certain embodiments, a powered injector may include at least one detecting device, sensor, or reader for identifying and obtaining information from the visible or invisible QR code 22. For example, the injector may include at least one dedicated sensor positioned to read the QR code 22. A sensor 152 for detecting and reading a QR code 22 is depicted on the injector illustrated in FIG. 2. The sensor 152 may also include a source of near infrared light or other appropriate electromagnetic radiation for illuminating an invisible QR code, thereby allowing the sensor to automatically read the QR code and to extract information therefrom. The QR code 22 may include information, such as, the type of syringe loaded into the injector, the size of syringe, date and time of manufacturer, brand authentication, batch number, lot number, recommended procedure or protocol, liability and warranty information, or any combination thereof. The QR code 22 could also serve as a pointer, taking a user to a website or data source with additional information about the type of injection being performed. The QR code may also serve as an authentication means for the syringe. For example, the injector may be configured to operate only when a syringe having a QR code 22 with the correct information is being used. The injector may be blocked from operation when an operator attempts to use a syringe without the correct QR code, since non-authorized syringes may not meet quality control or physical requirements for a specific injector or injection procedure.

According to various embodiments, the nanoparticles used to form the invisible QR codes 22 may be chemically and mechanically stable and capable to withstand stresses and strains associated with being placed on flexible surfaces. Thus, invisible QR codes 22 can be easily printed directly to glass, flexible plastic film, paper labels, and the like. The fact that the QR code 22 may be invisible means that it does not interfere with the aesthetic design of the product or product packaging. Additionally, injector operating systems may be programmed such that counterfeit syringes without the invisible QR code 22 will not be accepted by the injector. Therefore, the QR code 22 serves as a protection against syringes manufactured by unapproved entities, potentially without the necessary control standards.

In a further embodiment, a color changing pigment may be provided directly in the structure of the syringe itself. For example, thermochromic pigments (microcapsules) may be provided in the polymer used to manufacture the syringe. Syringes are generally manufactured by injection molding, though syringes manufactured by other molding process are also known in the art. The thermochromic pigment may also be applied to the outside of the syringe during or after syringe molding. The thermochromic pigments changes color when exposed to heat. For example, a syringe formed from the pigments may initially have a blue color. The syringe may become colorless and transparent as temperature increases. The process may be reversible, so that the syringe color returns to blue as temperature decreases. The color change may also be irreversible. Alternatively, nanocrystals and other stable fluorescent molecules, compounds or particles, as described herein, may be molded into a polymeric material during injection molding of the syringe, tubing set component, and/or vial/bag to provide a syringe, tubing set component, and/or vial/bag having a polymeric body incorporating the at least one tracer compound. Thus, syringe identification may be achieved by irradiating the syringe body with electromagnetic radiation having at least one first wavelength and detecting the emission of electromagnetic radiation having a specific at least one second wavelength. Various combinations of nanocrystals having different absorption and emission wavelengths may be incorporated into the syringe plastic to provide a multitude of unique combinations for detection of specific syringes, for example providing a code for identification of the syringe and various properties of the syringe.

As in the variously described embodiments, the injector may include a light source and at least one sensor for measuring the initial color of the pigment, for example after irradiation at an appropriate wavelength. For example, if the sensor detects a blue-colored syringe having the required emission wavelengths, the injection is permitted to begin. In particular embodiments, during the injection, the light source may generate heat, causing the microcapsules of the polymer syringe to become colorless. In the case of syringes with irreversible color change, the color change may serve as a safety features that prevents reuse of the syringe. The used colorless syringe is discarded. In embodiments, the colorless syringe cannot be reused since the injector may be configured to only accept syringes that are, for example, blue in color. Similarly, standard clear syringes manufactured by unapproved entities may also be rejected by the injector.

In a further embodiment and with continued reference to FIG. 4, microdots and micro-labels may be printed or laser-etched to the surface of the syringe barrel for proper identification. Microdots are microscopic particles, which are typically about one thousand microns in size and include alpha-numeric sequences. The microdots may be printed or laser-etched to a surface to form a barcode-like structure. Various sensors may be used to extract data about the barcode-like structure.

In certain embodiments, a microdot pattern 24 may also be molded onto a specific location on the syringe surface. The location of the microdot pattern 24 on the syringe surface may be used to convey useful information about the syringe. For example, placement of the microdot pattern 24 on different locations on the syringe barrel 12 may uniquely identify different type of syringes or different syringe volumes.

Additionally, microdots can include voids within molded dots that reflect various wavelengths of light in readily identifiable patterns. The injector may include a light source at a specific wavelength and sensors configured to measure the predefined reflection. The type of reflection could be used to provide additional information about the syringe or fluid solution. The information may be used for identification and authentication purposes In a further embodiment, a near field communication (NFC) antenna, such as a radio frequency identification (RFID) tag, may be adhered to the syringe body. RFID tags use a rectifying antenna (rectenna), which converts radio waves into electrical energy. The electrical energy is used for wireless transmission of data by radio waves. RFID tags can be printed onto plastic films, which can be adhered to the syringe barrel. The RFID tag can be used to transmit information about the syringe and fluid to a sensor, such as an RFID transmitter, data collection device, or other electronic controller. The information from the RFID tag can be used for identification and authentication purposes.

In a further embodiment, the syringe 10 may include microtracer compounds added to the polymer resin used to form the syringe 10. A reader, such as an ultraviolet or infrared light source, incorporated into the injector, allows for reading of the microtracer particles. The injector may be configured to operate only if the correct concentration and type of microtracer particles are identified. Thus, the injector can only be used with the correct type of approved syringes.

In a further embodiment, a gelatinous capsule or tablet encapsulating at least one tracer compound may be placed in a syringe barrel 12 of the syringe 10. The capsule or tablet dissolves or mixes with the fluids to be injected as the fluid to be injected is introduced to the syringe barrel 12. Once the capsule or tablet dissolves, the at least one tracer compound solubilizes or suspends in fluid solution and can be identified by the at least one sensor (such as sensors 152 depicted in FIG. 2) located in the syringe 10, injector, or fluid path set. The sensors may be configured to obtain information about the syringe 10 and fluid being injected, including the type of fluid, fluid concentration, type of syringe, or syringe volume. In another embodiment, the capsule or tablet may be integrally formed with or attached within a fluid path set of a fluid delivery system. In that case, the capsule or tablet dissolves when fluid is flushed through the fluid path set. The at least one tracer compound is identified by the at least one sensor on the fluid path set or on the patient. In a further embodiment, the tracer compound may be deposited on a surface contacted by the fluid, such as an inner surface of an element of the at least one fluid path, for example, a syringe, a tubing set, or a spike or needle. Such tracer compounds may then dissolve or be suspended in the fluid as the syringe is filled or as the fluid flows through the tubing set. By this way, the tracer compound is dissolved in or suspended in the fluid prior to injection into the patient.

In certain further embodiments, the syringe 10 and/or fluid path set may include means for automatically agitating or mixing the at least one tracer compound and fluid to be injected by, for example, vibration, rotation, or similar mechanical manipulation of the syringe and/or fluid path set. The manipulation means are useful for ensuring that the dissolved, broken, or mixed capsule or tablet containing the tracer compound is homogenously mixed throughout the fluid to be injected. Ensuring that the at least one tracer compound is homogenously mixed throughout the fluid ensures that the at least one tracer compound may be readily identified by the at least one sensor.

Similarly, in further embodiments, the at least one tracer compound may be enclosed within a rupture capsule or zone affixed to or integrally formed with an inner surface of the syringe barrel 12. The rupture capsule or zone may be configured to break, dissolve, or mix with the at least one tracer compound when positive or negative pressures or forces are applied by the rupture capsule or zone within the syringe. Positive or negative forces are present during filling and purging of the syringe 10. The rupture capsule or zone may also be placed in the fluid path set, and may rupture when fluid is flushed through the fluid path set.

Figure 5A:
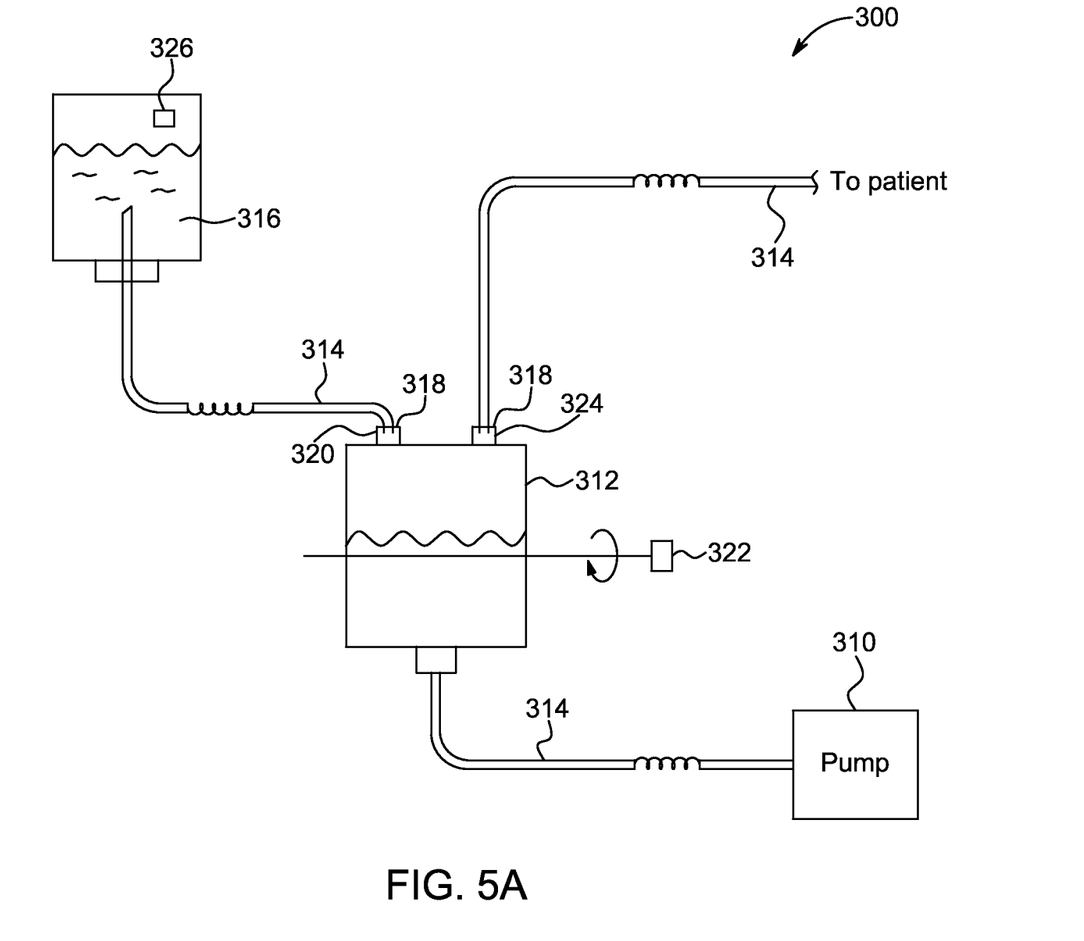
FIG. 5A is a schematic drawing of a fluid delivery system including a fluid container, according to an embodiment.

According to a further aspect and with reference to FIG. 5A, a fluid delivery system 300 is provided. Generally, the system 300 includes a pump 310, a fluid container or reservoir, such as a three-port temporary fluid container 312, bounded tube sets 314, and a prefilled contrast pouch 316. The prefilled contrast pouch 316 contains a fluid contrast agent for delivery to a patient. Thus, the pouch 316 functions as a replacement for traditional syringes or containers as are known in the art. In use, the pump 310 pulls contrast out of the prefilled contrast pouch 316 and into the temporary fluid bag 312 through a one-way check valve 318 and fluid entry port 320. The check valve 318 may be integral to the port 320 or may be a separate structure in the tube set 314. Once the contrast is drawn into the temporary fluid bag 312, a mechanism 322 rotates the temporary fluid bag 312 upside down to allow the contrast contained therein to flow toward the other side of the bag 312 by gravity. When the bag 312 is in the upside down position, the pump 310 action is reversed, so that the pump 310 forces contrast from the temporary fluid bag 312 through a patient port 324, located opposite the fluid entry port 320. Contrast is prevented from returning to the contrast pouch 316 by the one-way check valve 318 located near the entry port 320. The patient port 324 may also include a check valve 318 to permit fluid flow out of the fluid bag 312 and to prevent fluid from reentering the fluid bag 312 through the patient port 324.

Figure 5B:
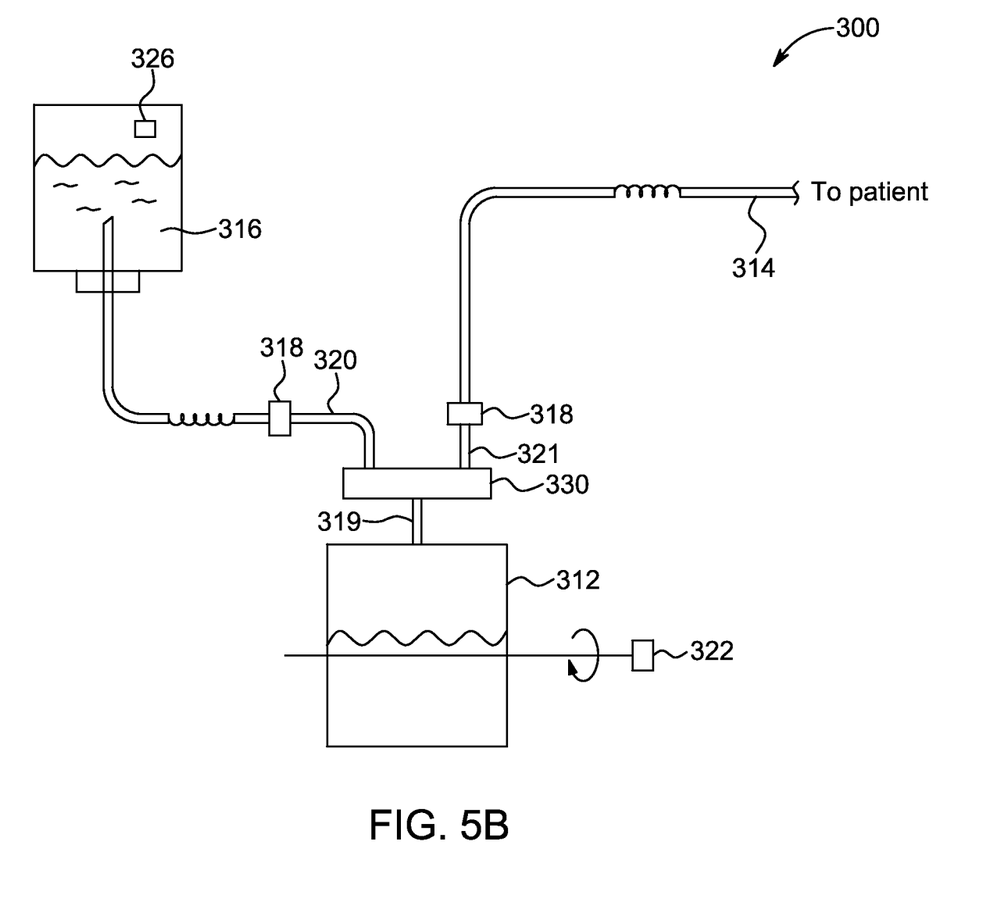
FIG. 5B is a schematic drawing of a fluid delivery system including a fluid container, according to an embodiment.

With reference to FIG. 5B, an alternative embodiment of a fluid delivery system 300 is illustrated. In the system 300, a pump 330 actively pushes fluid into the bag 312 through check valves 318. The pump 330 may be a peristaltic pump, piston or syringe pump, diaphragm pump, or rotary pump. The pump 330 could have a separate inlet 320 and outlet 321. Alternatively, the outlets 320, 321 could be combined into one inlet/outlet, with the direction being controlled by the direction of the pump 330 and the check valves 318. Alternatively, a stopcock (not shown) could be used to control whether fluid is drawn from fluid pouch 316 or delivered to patient via tubing set 314. Alternatively, two separate pumps (not shown) could be used. For example, a first pump may pull the fluid from pouch 316 and delivers it into fluid container 312. When ready, a second pump would then pull fluid from container 312 and deliver it to the patient via tubing 314. Other pumping mechanisms, fluid containers, and arrangements of valves and tubing, as are known in the art, may also be used within the scope of the present disclosure. For example, in a non-limiting embodiment, the fluid container 312 is a syringe and pump 330 is an injector head.

The above described system 300 offers certain advantages compared with other known fluid delivery systems. Particularly, the system eliminates multiple preparation steps. The contrast agent is prepared without needing to connect and disconnect various syringes and tubes from each other prior to injection. The temporary fluid bag 312 and tube sets 314 may also be provided in a preassembled state to provide an even more integrated solution. In that case, the operator needs only to hook up the contrast pouch 316 and connect the pump 310 prior to use.

As in the previously described embodiments, the contrast pouch may include a QR code 326 or other indicia for authentication and information purposes. The QR code 326 prevents counterfeit products. The QR code 326 also provides information about the contrast media (e.g. type, contrast amount, recommended procedure, warranty information, etc.) for the operator. Having such information readily available reduces the possibility of user error.

In a preferred embodiment of the system 300, a tracer or colorant may come premixed with the contrast in the prefilled contrast pouch 316 or fluid in the temporary fluid bag 312. Premixing the tracer or colorant has the benefit that concentration can be controlled during manufacturing. Alternatively, the tracer could be associated with one or more of the fluid path elements. For example, a powder or liquid tracer or colorant may be provided in or on walls of the tube set 314, fluid bag 312, or a syringe. Including the tracer on or in a fluid path element has several benefits. First, the tracer is mixed with the fluid for a relatively short time. Additionally, the tracer can be used with fluids from various manufacturers. Another benefit is that one or more system sensors can be placed in the fluid path elements and adapted to tell when the tracer has been removed from the fluid path element. This feature would prevent use beyond a prescribed usage pattern. This method of preventing reuse is similar in concept to toothbrushes with fibers that change color after prolonged use. One disadvantage to this method is that the concentration of the tracer can vary from use to use, or over time, as the tracer moves into the liquid, unless all of the tracer is removed in the first use and the fluid path is designated for single use only. The variation in the concentration of the tracer can be compensated for by having additional sensor elements that periodically or continually measure a property of the separate fluids, as well as, one or sensors that measure a property of the combined fluid.

It is noted that the rate of movement of the tracer or colorant into the liquid can be controlled by various means, such as diffusion, dissolution, coating, porosity, and other mechanisms known to those skilled in the art. Changes in concentration of the tracer can be used to monitor the use of the fluid path elements and/or the volume of the fluid which has been moved through the element. For example, in the system 300 of FIG. 5A, the bag 312 could contain the tracer as a powder. Pulling the contrast, saline, or other solution into the bag 312 and then agitating it sufficiently would provide a relatively uniform mixture for subsequent use.

Although the disclosure has been described in detail for the purpose of illustration based on what are currently considered to be the most practical and preferred embodiments, it is to be understood that such detail is solely for that purpose and that the disclosure is not limited to the disclosed embodiments, but, on the contrary, is intended to cover modifications and equivalent arrangements. For example, it is to be understood that the present disclosure contemplates that, to the extent possible, one or more features of any embodiment can be combined with one or more features of any other embodiment. In addition to the absorption and emission of light of various wavelengths, other magnetic or electromagnetic properties and sensors may form the basis of the sensing phenomena. For example, the properties may include permeability, permittivity, conductivity, and complex permeability. Additionally, ultrasound energy may be used with appropriate tracer materials.

We claim:

1. A system for injection of a fluid into a patient, the system comprising:
    a fluid to be delivered to a vein or artery of the patient having at least one active compound;
    an injector, a fluid container, and a fluid path set configured to deliver the fluid having the at least one active compound to the vein or artery of the patient;
    a powder comprising at least one tracer compound disposed on inner walls of the fluid container or the fluid path set configured to mix with the fluid comprising the at least one active compound as it passes through the fluid container and/or the fluid path set, thereby forming a mixed fluid to be delivered to the vein or artery of the patient comprising the at least one active compound and the at least one tracer compound;
    at least one sensor configured to be coupled to at least one of the fluid path set, the injector, and the patient, the at least one sensor comprising an electromagnetic radiation source and an electromagnetic radiation detector, wherein the at least one sensor is configured to measure electromagnetic radiation of the at least one tracer compound in the mixed fluid; and
    a controller configured to:
        receive at least one measurement for the electromagnetic radiation from the at least one sensor; and
        adjust an injection flow rate of the injector or concentration of the fluid to be delivered to the vein or artery of the patient in real time based on the at least one measurement from the at least one sensor,
        wherein the at least one tracer compound comprises at least one nanoparticle capable of absorbing electromagnetic radiation from the electromagnetic radiation source and emitting the electromagnetic radiation that can be detected by the electromagnetic radiation detector of the at least one sensor.

2. The system of claim 1, wherein the electromagnetic radiation source of the at least one sensor emits electromagnetic radiation having at least one first wavelength and the electromagnetic radiation detector of the at least one sensor is configured to measure electromagnetic radiation having at least one second wavelength,
    wherein the at least one nanoparticle comprises at least one up-converting fluorescent nanocrystal,
    wherein the at least one up-converting fluorescent nanocrystal comprises a compound that absorbs two or more low-energy photons having the at least one first wavelength in an infrared region of an electromagnetic spectrum and emits at least one higher energy photon having the at least one second wavelength in a visible region of the electromagnetic spectrum,
    wherein the at least one second wavelength is in the green or blue region of the visible spectrum, and
    wherein the higher energy photon can penetrate through at least a portion of a tissue of the patient.

3. The system of claim 1, wherein the at least one active compound comprises a therapeutic agent or drug, and wherein the nanoparticle is substantially inert to biological systems and has at least one of a size and a shape below a renal threshold for excretion.

4. The system of claim 1, wherein the at least one sensor is configured to be coupled to a tissue section of the patient to detect the electromagnetic radiation from the at least one sensor to determine a location of the tracer within the vein or artery of the patient.

5. The system of claim 1, wherein the controller is configured to adjust the injection flow rate of the injector by decreasing the injection flow rate from an initial flow rate to a decreased flow rate or increasing the injection flow rate from the initial flow rate to an increased flow rate.

6. The system of claim 1, wherein the fluid container comprises at least one syringe comprising a cylindrical barrel and a plunger positioned in the cylindrical barrel, wherein the powder comprising the at least one tracer compound is on an inner wall of the cylindrical barrel of the at least one syringe, and
 wherein the injector comprises an external powered injector operatively connected to the plunger of the at least one syringe, such that upon activation, the powered injector moves the plunger through the cylindrical barrel of the at least one syringe to deliver the mixed fluid comprising the at least one active compound and the at least one tracer to the artery or vein of the patient through the fluid path set.

7. The system of claim 6, wherein the system comprises at least two syringes comprising plungers operatively connected to the external powered injector, and wherein a first syringe contains the fluid having the at least one active compound and the powder comprising the at least one tracer compound, and a second syringe contains saline or other flushing fluid.

8. The system of claim 1, wherein the at least one sensor is configured to detect extravasation of the fluid from the vein or artery of the patient to surrounding tissue, and wherein the controller is configured to adjust the injection flow rate or concentration of the at least one active compound in the mixed fluid to be delivered to the vein or artery of the patient when the extravasation of the fluid is detected.

9. The system of claim 1, wherein the injector comprises at least one of a peristaltic pump, a diaphragm pump, or a rotary pump.

10. The system of claim 1, wherein the at least one sensor is connected to the injector or the fluid path set and is configured to detect movement of the mixed fluid having the at least one active compound and the at least one tracer compound through the fluid path set.

11. The system of claim 1, wherein the controller is configured to adjust the concentration of the at least one active compound in the mixed fluid to be delivered to the vein or artery of the patient by increasing the concentration of the at least one active compound of the mixed fluid to be delivered from an initial concentration to an increased concentration or decreasing the concentration of the at least one active compound in the mixed fluid to be delivered from the initial concentration to a reduced concentration.

12. A method for controlling injection of a fluid in a vascular system of a patient, the method comprising:
 advancing a plunger through a cylindrical barrel of a syringe, with at least one of a manual or an automatic fluid injector, to expel a fluid comprising at least one active compound from the syringe to a fluid path set in fluid communication with the syringe and with a vein or artery of the patient, the fluid path set comprising a powder comprising at least one nanoparticle tracer compound disposed on inner walls of the fluid path set, thereby mixing the fluid comprising the at least one active compound with the at least one nanoparticle tracer compound to form a mixed fluid to be delivered into the vein or artery of the patient through the fluid path set;
 associating at least one sensor with a tissue section of the patient, wherein the tissue section is adjacent to a portion of vasculature of the patient, and wherein the at least one sensor comprises an electromagnetic radiation source for emitting electromagnetic radiation having at least one first wavelength and an electromagnetic radiation detector for detecting electromagnetic radiation having at least one second wavelength;
 irradiating the tissue section with the electromagnetic radiation having the at least one first wavelength from the electromagnetic radiation source;
 measuring the electromagnetic radiation having the at least one second wavelength using the electromagnetic radiation detector;
 determining a location of the electromagnetic radiation having the at least one second wavelength in the vasculature of the patient from the measured electromagnetic radiation; and
 adjusting an injection flow rate of the fluid injector or a concentration of the fluid to be delivered to the vasculature of the patient in a real time manner based on the measured electromagnetic radiation having the at least one second wavelength.

13. The method of claim 12, wherein the at least one nanoparticle tracer compound comprises at least one up-converting fluorescent nanocrystal and the at least one active compound comprises a contrast agent.

14. The method of claim 12, further comprising determining from the measured electromagnetic radiation having the at least one second wavelength one or more of a flow rate of the at least one active compound in the vasculature of the patient, a direction of flow of the at least one active compound in the vasculature of the patient, a presence of air in the vasculature of the patient, a presence of extravasation of the at least one active compound, a volume rate of the at least one active compound in the vasculature of the patient, a bolus sharpness of the injected fluid, a value for an estimated glomerular filtration rate, and combinations of any thereof.

15. The method of claim 12, wherein adjusting the injection flow rate of the fluid injector comprises increasing the injection flow rate of the injector from an initial flow rate to an increased flow rate or decreasing the injection flow rate of the injector from the initial flow rate to a decreased flow rate.

16. A system for injection of a fluid into a patient comprising:
 a first syringe comprising a first cylindrical barrel and a first plunger positioned in the first cylindrical barrel, the first syringe containing a fluid comprising contrast media;
 a second syringe comprising a second cylindrical barrel and a second plunger positioned in the second cylindrical barrel, the second syringe containing a flushing solution comprising saline in the second cylindrical barrel of the second syringe;
 an injector operatively connected to the first plunger of the first syringe and the second plunger of the second syringe, configured to advance the first and second plungers through the first and second syringes to expel the fluid and the flushing solution from the first syringe and the second syringe, respectively;
 a fluid path set in fluid communication with the first syringe and the second syringe, the fluid path set comprising: a y-connector for mixing fluids from the first syringe and the second syringe, the y-connector comprising first and second proximal ends connected to the syringes by one or more input lines and a distal end connected to a connector conduit; a powder disposed on inner walls of the fluid path set comprising at least one up-converting fluorescent nanocrystal; and a catheter or needle cannula connected to the connector conduit wherein the fluid from the first syringe and the flushing solution from the second syringe mix with the powder comprising the at least one up-converting fluorescent nanocrystal to form a mixed fluid comprising the contrast media, the at least one up-converting fluorescent nanocrystal, and the flushing solution, the mixed fluid being configured to be delivered to a vein or artery of the patient through the catheter or needle cannula;

at least one sensor configured to be coupled to a tissue section of the patient, wherein the at least one sensor is configured to measure at least one property of the fluorescent nanocrystal in the mixed fluid selected from the group consisting of a concentration of the fluorescent nanocrystal at a site within the patient near the tissue section, a location of the fluorescent nanocrystal within a vascular system of the patient near the tissue section, an extravasation of the fluorescent nanocrystal outside the vascular system of the patient near the tissue section, a flow rate or flow direction of the fluorescent nanocrystal in the vascular system of the patient near the tissue section, a bolus sharpness of the fluid in the vascular system of the patient near the tissue section, a value for an estimated glomerular filtration rate, and combinations of any thereof; and a controller configured to:
receive measurements for the at least one property of the fluorescent nanocrystal from the at least one sensor; and
adjust an injection flow rate of the injector or a concentration of the contrast media in the mixed fluid to be delivered to the vein or artery of the patient based on the received measurements from the at least one sensor.

17. The system of claim 16, wherein the injector comprises an external powered injector that expels the fluid from the first syringe and the solution from the second syringe into the one or more input lines of the fluid path set, and
wherein the controller is configured to adjust the injection flow rate of the injector by adjusting a speed at which the first plunger of the first syringe is advanced through the first cylindrical barrel of the first syringe or the second plunger of the second syringe is advanced through the second cylindrical barrel of the second syringe.

18. The system of claim 16, wherein the controller is configured to adjust the injection flow rate of the injector by increasing the injection flow rate of the injector from an initial flow rate to an increased flow rate or decreasing the injection flow rate of the injector from the initial flow rate to a decreased flow rate.

19. The system of claim 16, further comprising a second sensor connected to the fluid path set configured to detect the fluorescent nanocrystal in the mixed fluid passing through the fluid path set, and wherein the controller adjusts the injection flow rate or the concentration of the contrast media in the mixed fluid based, in part, on measurements by the second sensor.

* * * * *